United States Patent
Chu

(10) Patent No.: US 7,140,879 B2
(45) Date of Patent: Nov. 28, 2006

(54) SOFT SALIVA EJECTOR

(75) Inventor: William Hui-Kang Chu, 2591 Meadowview Ct., Rochester Hills, MI (US) 48306-3823

(73) Assignee: William Hui-Kang Chu, Hickory, NC (US)

( * ) Notice: Subject to any disclaimer, the term of this patent is extended or adjusted under 35 U.S.C. 154(b) by 156 days.

(21) Appl. No.: 10/840,556

(22) Filed: May 6, 2004

(65) Prior Publication Data

US 2005/0250071 A1 Nov. 10, 2005

(51) Int. Cl.
*A61C 17/08* (2006.01)
(52) U.S. Cl. .......................................... 433/91; 433/96
(58) Field of Classification Search ............. 433/91–96
See application file for complete search history.

(56) References Cited

U.S. PATENT DOCUMENTS

| | | | | |
|---|---|---|---|---|
| 1,698,331 | A | * | 1/1929 | Gunter ..................... 433/94 |
| 3,758,950 | A | * | 9/1973 | Krouzian ................... 433/91 |
| D247,574 | S | * | 3/1978 | Orsing ..................... D24/112 |
| 5,066,228 | A | * | 11/1991 | Doundoulakis et al. ....... 433/91 |
| 6,022,326 | A | * | 2/2000 | Tatum et al. ............... 600/573 |
| 6,280,415 | B1 | * | 8/2001 | Johnson ..................... 604/118 |

* cited by examiner

*Primary Examiner*—Cris L. Rodriguez
*Assistant Examiner*—Patrick J. Kilkenny

(57) ABSTRACT

A soft disposable ejector tip 2 that can match the various contour of the mouth cavity is attached to a chamfer shape copper wire reinforced tube end 3. This tube is attached to a metal holder with finger control level to regulate the negative vacuum pressure needed to extract saliva or spray water inside the mouth during dental works.

1 Claim, 2 Drawing Sheets

Ejector Tip 2 Side View

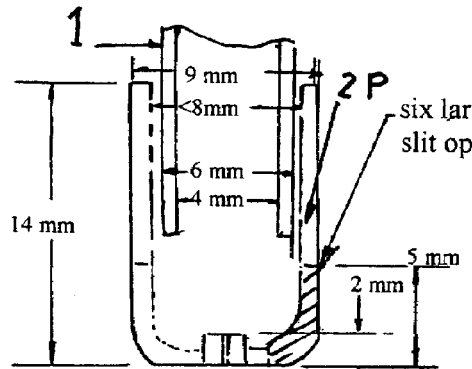
FIG.1 Prior Art (PR) side View
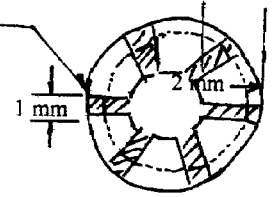
FIG. 2 PR Bottom View
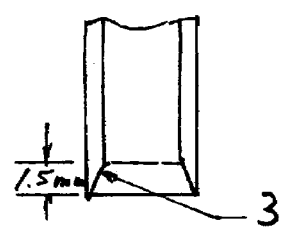
FIG.3 Tube With Chamfer End
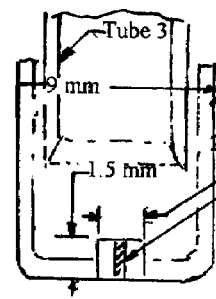
FIG.4 Ejector Tip 2 Side View
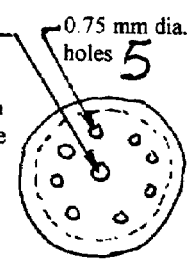
FIG.5 Ejector Tip Bottom View
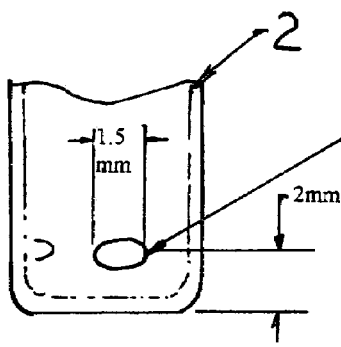
FIG.6 Ejector Tip Side View With Eight Rounded Slit Openings
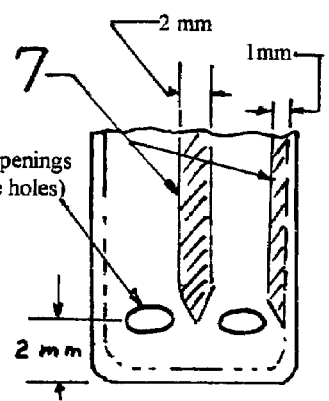
FIG.7 Wall Reinforcements

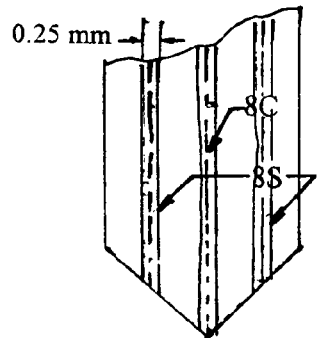
FIG. 8 Grooves in Wall Reinforcements
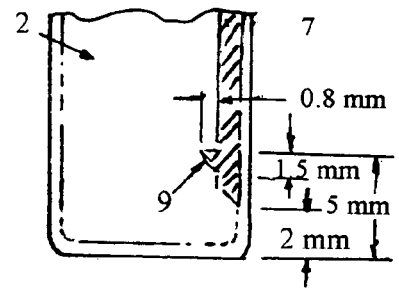
FIG. 9 Tube Stop
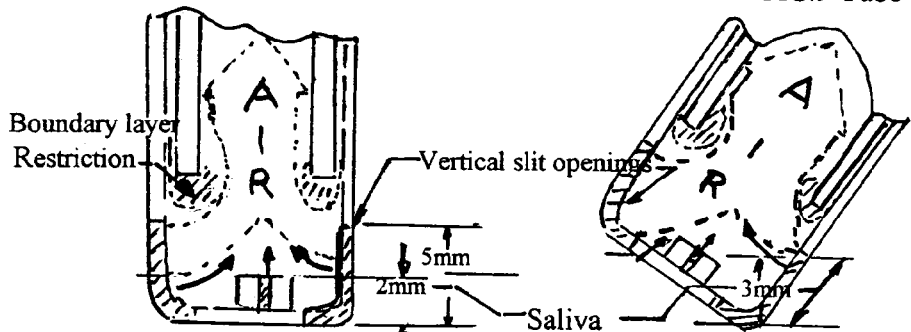
FIG. 10 Air (--->) and Saliva Flow (—>) Schematic Prior Art, Straight and Slanted
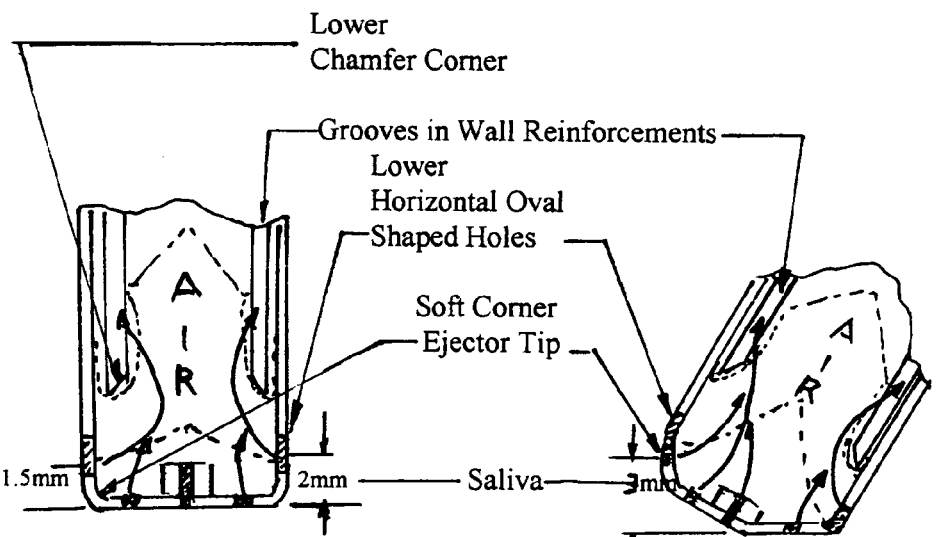
FIG. 11 Air (--->) And Saliva Flow (—>) Schematic Ejector Tip, Straight and Slanted

SOFT SALIVA EJECTOR

TECHNICAL FIELD

This invention will increase the productivity of dentist and hygienist so that the ejector does not have to be constantly repositioned to remove the saliva in the mouth cavity during dental works. It will have a minimum noise increase when any of the substances is entering into the ejector and the tube. The ejector and the tube assembly are disposable after use.

BACKGROUND OF THE INVENTION

FIGS. 1 and 2 show the current ejector used by most dentists. It consists of a straight tube item 1 and the Prior Art tip 2P which is about 9 mm outside diameter, less than 8 mm inside diameter and 14 mm long with six very thick reinforced slit openings at the lower side and one tiny bottom hole 2 mm above the contact surface. Each of these six slit openings is 5 mm long and 1 mm wide from side view and is also opened at the bottom for about another 2 mm, an area too big to prevent soft tissue aspiration. The tip is very hard at the corner area.

The copper reinforced tube has a outer diameter about 6 mm and inner diameter of 4 mm or a inside air flow area about 12 mm square. The net air passage cross section area from the six slit openings, the bottom hole and the surrounding gaps between the tube 1 and the tip 2P is estimated at two to three times of 12 mm square. Air being sucked into the slit openings at the top 2 or 3 mm range can fill the air flow volume inside the tube without providing any interaction or suction at the bottom 1 or 2 mm range for the saliva to jump through the air and move into the tube. Fortunately, if the tip is placed at the right place, it can be pressed into the soft tissue making the saliva level at 1 to 3 mm above the hard bottom of the tip readied to be sucked into the ejector via three vertical wall reinforcements acts as the tube and tip mating stoppers. However, if the tip is loosely left inside the mouth and not pressing down against the soft tissue, as during deep cleaning, then a 1 or 2 mm rise of liquid level would NOT be sucked into the tube when the ejector tip is perpendicular to the tissue surface, and 2 to 3 mm if it is at an angle. These liquid substances would then flow toward the throat area and causes the patient to choke; regardless what the vacuum pressure level is set at the finger controlled metal handle.

DESCRIPTION OF THE INVENTION

This invention solves all the above problems and consists of two major parts. First, FIG. 3 shows the new main tube to ejector tip interface. The wire support inside the tube is 1.5 mm shorter so the tube end can have a chamfer shape 3 when it mates with the ejector tip. This configuration with the same down draft air flow pattern between the tube and the ejector wall significantly decreases the boundary layer resistances and increases the net up draft power at the bottom of the soft ejector interior. See FIGS. 10 and 11.

Second, the new ejector tip has a much softer corner made of 0.6 mm thick of plastic material.

FIG. 4 is the side view of the new tip. The bottom 3-mm high ejector material, due to its thin thickness and many holes is very easy to conform to any contour when it is left inside the mouth without downward pressure. The center hole 4 at the bottom is about 1 mm in diameter. This hole is molded from a 2 mm-diameter disk, about 1.5 mm from the very bottom of the tip.

FIG. 5 shows eight additional holes 5 each is 0.75 mm diameter as view from the top of the new ejector 2.

FIG. 6 is the side view of the new ejector tip. Eight additional horizontally rounded slit openings 6 at 2 mm above the bottom and centrally lined up from the eight holes 5, provide most of the air intake space needed into the ejector. Each rounded slit is 0.5 mm in radius and 1.5 mm long. The total opening area of the new tip from the holes 5 and rounded slits 6 is about 13.5 mm square or just slightly larger than the tube cross section area FIG. 7 shows eight vertical side wall reinforcements 7, between the eight rounded slit openings 6. Each is approximately 2.0 mm wide at the top of the inner ejector surface and 1 mm thick at the top, is tailored to a pointed edge flatten to the normal wall thickness between each of the eight rounded slit openings 6, at 2 mm above the bottom.

FIG. 8 shows each of item 7 have three V-shape grooves 8. Each of the grooves is approximately 0.25 mm wide at the surface opening and a depth of 0.2 mm. The longest groove is at the center mark as 8c and other two grooves mark as 8s.

FIG. 9 shows the four tube stoppers 9 inside the new ejector tip. Each of the four stoppers, at every other of wall reinforcements 7 is molded from the same side wall material, same width 2.0 mm wide approximately 0.8 mm flat out of the reinforcement wall, 5 mm from the very bottom of the ejector tip 2 and triangularly down to the wall at a depth of 1.5 mm.

FIG. 10 shows the lack of interaction of air and saliva flows in the Prior Art item 2P.

FIG. 11 shows the much improved interaction due to the new chamfer shape tube end 3 and the much lower level air intake from the bottom holes 5 and side rounded slit openings 6, which enhances the net up draft of very low level of liquid near the very bottom of the ejector tip 2, whether it is left straight or slanted inside the mouth.

DESCRIPTION OF OPERATION

This ejector tip is very soft but durable and user friendly. It can easily match the contour of the surface where it is left inside the mouth and provide a much better vacuum action of low level liquid near the bottom of the ejector tip 2. Air or liquid being sucked into the eight rounded horizontal slit openings 6 are at a very low level which blows and pushes the liquid upward into the tube via surface tension and capillary action through the eight reinforced walls 7 each with three grooves 8c and 8s. The continuous vacuum action can extract the very low level of saliva or water with the ejector tip 2 just barely contacting the surface wherever it is left inside the mouth, with minimum noise increase especially during deep cleaning dental works.

I claim:

1. A disposable soft saliva ejector comprising:

A plastic tube with one chamfered end inserted into a pliable ejector tip, the other end attached to a vacuum source;

said ejector tip is made of plastic material and has a cylindrical cup shaped wall and comprises a center hole at the distal end of the ejector tip surrounded by eight evenly spaced holes of smaller diameter than that of the center hole;

said ejector tip further comprises eight oval shaped holes evenly spaced on a circumferential line along the ejector tip wall proximal to the distal end of the ejector tip;

said ejector tip further comprises interior vertical wall reinforcements located between each oval hole;

the thickness of said wall reinforcements taper from the top of the ejector tip to a level flush with the internal surface of the ejector tip at the distal end of the wall reinforcement adjacent to the oval holes;

said wall reinforcements comprise three evenly spaced V-shaped grooves that run the length of the wall reinforcements;

said wall reinforcements further comprise a wedged shaped tube-stop projecting from the wall reinforcement into the interior of the ejector tip;

said tube stops located along a circumferential line above the oval holes.

\* \* \* \* \*